United States Patent [19]
Donis et al.

[11] Patent Number: 6,001,613
[45] Date of Patent: Dec. 14, 1999

[54] PLASMID BEARING A CDNA COPY OF THE GENOME OF BOVINE VIRAL DIARRHEA VIRUS, CHIMERIC DERIVATIVES THEREOF, AND METHOD OF PRODUCING AN INFECTIOUS BOVINE VIRAL DIARRHEA VIRUS USING SAID PLASMID

[75] Inventors: Ruben O. Donis; Ventzislav B. Vassilev, both of Lincoln, Nebr.

[73] Assignee: Board of Regents of University of Nebraska, Lincoln, Nebr.

[21] Appl. No.: 08/859,694

[22] Filed: May 21, 1997

Related U.S. Application Data

[60] Provisional application No. 60/018,246, May 24, 1996.

[51] Int. Cl.$^6$ .............................. C12N 15/00; C12N 7/00
[52] U.S. Cl. ................. 435/91.4; 435/91.21; 435/91.33; 435/235.1; 435/320.1
[58] Field of Search .................................. 435/69.3, 70.3, 435/91.1, 91.21, 91.33, 91.4, 235.1, 320.1; 536/23.1, 23.72

[56] References Cited

U.S. PATENT DOCUMENTS

| | | | |
|---|---|---|---|
| 4,719,177 | 1/1988 | Baltimore et al. | 435/91 |
| 4,992,367 | 2/1991 | Cullen | 435/69.52 |
| 5,206,163 | 4/1993 | Renard et al. | 435/240 |
| 5,670,152 | 9/1997 | Weiner et al. | 424/189.1 |

OTHER PUBLICATIONS

Brock et al., Journal of Virological Methods, 38:39–46, 1992.
Collett, et al., Virology, 165:191–199, 1988.
Ferrari, M., Microbiologica, 8:17–22, 1985.
Elaine T. Schenborn, et al., "A Novel Transcription Property of SP6 and T7 RNA Polymerases: Dependence on Template Structure," *Nucleic Acids Res.*, vol. 13, No. 17, 1985, pp. 6223–36.
Ruitang Deng, et al., "5' and 3' Untranslated Regions of Pestivirus Genome: Primary and Secondary Structure Analyses," *Nucleic Acids Res.*, vol. 21, No. 8, 1993, pp. 1949–1957.

*Primary Examiner*—Donna Wortman
*Assistant Examiner*—Brenda G. Brumback
*Attorney, Agent, or Firm*—Shook, Hardy & Bacon L.L.P.

[57] ABSTRACT

A plasmid bearing a cDNA copy of the genome of bovine viral diarrhea virus (BVDV), chimeric derivatives of the plasmid and a method of producing an infectious bovine viral diarrhea virus using the plasmid are disclosed. The invention relates to a plasmid DNA molecule that replicates easily in *E. coli* and contains a sufficient portion of the genome of BVDV, cloned as cDNA, to be a suitable template to produce RNA in vitro which, upon transfection into bovine cells, gives rise to infectious BVDV. The BVDV created by the process of the invention can be engineered for use as a vector in many advantageous applications.

21 Claims, 10 Drawing Sheets

Complete digestion SacI, partial digestion NdeI,. Fragment isolation, purification, CIAP treat.
Complete digestion SacI, partial digestion NdeI, Fragment isolation, purification, CIAP treat.
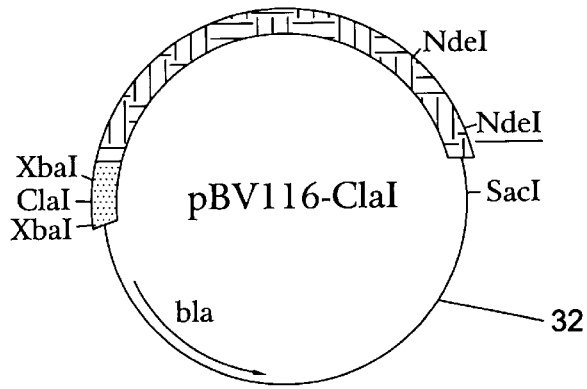
Fig. 6.
19
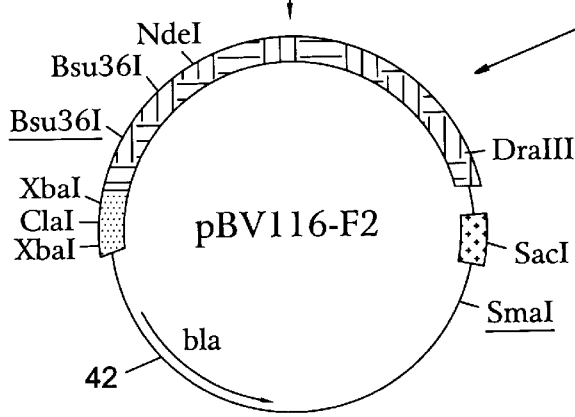
SmaI/Bsu36I - part. digested insert
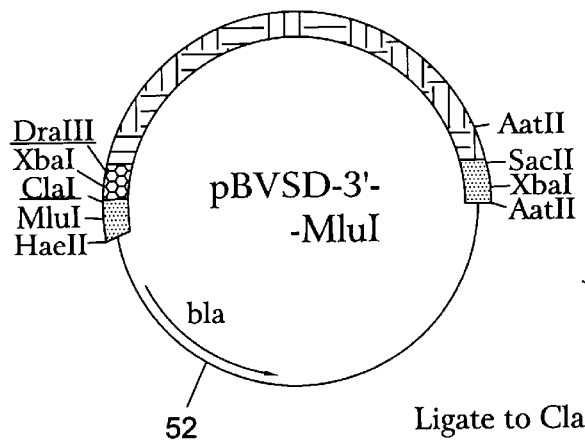
Ligate to ClaI/DraIII digested vector. CIAP.

Fig. 7.

| PLASMID | INSERT, SIZE | VECTOR | TOTAL |
|---|---|---|---|
| pBV 18 | 34-1308, 1274 bp | pUC 13 | 3954 bp |
| pBV 116 | 1111-3577, 2466 bp | pGEM 4 | 5337 bp |
| pBV D79 | 3061-4379, 1318 bp | pUC 9 | 3983 bp |
| pBV F2 | 4043-5181, 1138 bp | pUC 9 | 3803 bp |
| pBV SD2.3 | 5173-12542, 7369 bp | pGEM 4 | 9312 bp |

PLASMID BEARING A CDNA COPY OF THE GENOME OF BOVINE VIRAL DIARRHEA VIRUS, CHIMERIC DERIVATIVES THEREOF, AND METHOD OF PRODUCING AN INFECTIOUS BOVINE VIRAL DIARRHEA VIRUS USING SAID PLASMID

This application claims the benefit of U.S. Provisional Application No. 60/018,246 filed May 24, 1996.

RIGHTS IN THE UNITED STATES GOVERNMENT

This invention was made with federal support under NRI grant 92-37204-7959 from the USDA. The United States government has certain rights to the invention.

BACKGROUND OF THE INVENTION

This invention relates to plasmids for viruses, methods for engineering the plasmids and methods for analyzing virus replication.

The bovine viral diarrhea virus, or BVDV, is the prototype species in the Pestivirus genus of the Flaviviridae. Positive strand RNA viruses, such as the poliovirus and the BVDV, have a genome consisting of a single molecule of RNA. Pure RNA extracted from either highly concentrated and purified poliovirus or BVDV can be transfected into a susceptible cell, which results in the production of infectious progeny virus by the cell. A homogeneous preparation of viral RNA molecules is infectious upon transfection.

The usefulness of RNA molecules from BVDV and poliovirus is limited because they are many thousand nucleotides in length and cannot be engineered in vitro to change their sequence using current technology. By contrast, DNA molecules of similar length, cloned into plasmids, can be manipulated with restriction enzymes and synthetic oligodeoxynucleotides to obtain any desired sequence.

It is known that the entire RNA sequence of some viruses can be cloned into a plasmid. Such plasmids can be used to produce RNA molecules in vitro that mimic the properties of the RNA extracted from the purified virus. The RNA synthesized in vitro using a plasmid DNA as a template produces the virus upon transfection into susceptible cells. Plasmids with this property are known as "infectious clones."

BVDV remains enzootic in cattle populations throughout the world. Current vaccines are either relatively unsafe or ineffective in control and eradication programs. Efficient reverse genetics approaches using an infectious molecular clone of the BVDV genome may contribute to the development of rationally-designed safe and efficacious vaccines.

The construction of an infectious molecular clone of BVDV, its subsequent modification to introduce a sequence tagged site and the production of a chimeric virus expressing a surface glycoprotein from a different strain, manipulating the BVDV genome in vitro and its potential effectiveness for reverse genetic analyses of pestivirus are described hereinafter.

SUMMARY OF THE INVENTION

Accordingly, it is an object of the invention to provide a novel plasmid.

It is a further object of the invention to provide a novel method for engineering a plasmid.

It is a further object of the invention to provide a novel method for engineering the genome of BVDV for vaccine development.

It is a still further object of the invention to provide a novel method for the analysis of virus replication.

It is a still further object of the invention to provide a novel approach for vaccine development.

It is a still further object of the invention to provide a BVDV infectious clone.

BRIEF DESCRIPTION OF THE DRAWINGS

The above noted and other features of the invention will be better understood from the following detailed description, in which:

FIG. 7 is a table describing starting plasmids for the production of the chimeric virus of this invention.

DETAILED DESCRIPTION OF THE INVENTION

Figure 1:
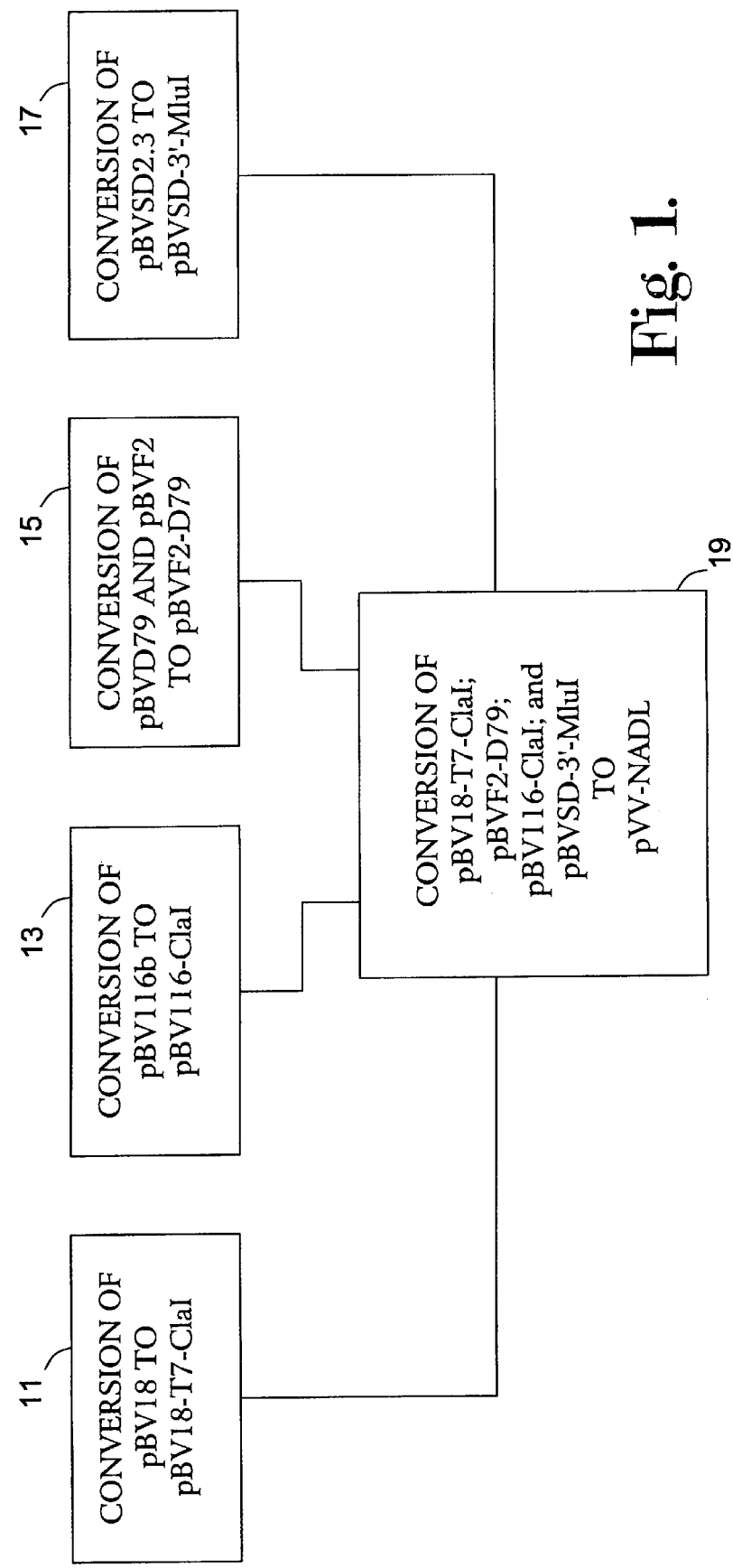
FIG. 1 is a block diagram illustrating the process of forming BVDV cDNA genomic clone.

The present invention relates to a plasmid DNA molecule that replicates easily in Escherichia coli bacteria and contains a sufficient portion of the genome of BVDV, cloned as cDNA, to be a suitable template to produce RNA in vitro, which upon transfection into bovine cells, gives rise to infectious BVDV. The BVDV created by this process can be engineered as a vector for use in the following applications:

(1) the development of attenuated or avirulent virus strains for use as live vaccines;

(2) the addition of foreign sequences encoding proteins of immunological interest, such as proteins from other parasites or viruses, such as foot and mouth disease, leading to the use of BVDV as a vector to vaccinate against other infectious or parasitic diseases;

(3) the addition of immunostimulatory molecules, such as C3d complement molecule interleukins and the like;

(4) the development of marker vaccines with a characteristic deletion which allows the discrimination between vaccinated and infected animals by retrospective serological tests;

(5) the development of sequence-tagged BVDV vaccines which allow identification of the origin of the BVDV in the event of alleged vaccine-associated outbreaks;

(6) the mapping of attenuating mutations leading to avirulent phenotypes; and (7) the identification of novel antiviral targets against pestivirus and related flaviviruses by creation of suitable chimeric viruses.

Five plasmids from the work of Collett et al., "Molecular Cloning and Nucleotide Sequence of the Pestivirus Bovine Viral Diarrhea Virus," *Virology* 165, 191–199, were used as a starting material for the present invention. Cultures of these plasmids are maintained in several private cultures, one of which is in the refrigerator (Room VBS 151) in the Veterinary Basic Science Building, Department of Veterinary Science, University of Nebraska, Lincoln, Nebr. 68583, designated: (1) pBV-18; (2) pBV-116b; (3) pBV-D79; (4) pBV-F2; and (5) pBVSD2-3'. These cultures will be made available upon granting of the patent. These plasmids are described in FIG. 7.

From these plasmids, six vectors have been constructed: (1) a plasmid containing a chimeric genome of BVDV, strain NADL, with Singer strain E2/gp53 glycoprotein, propagated in E. coli strain GM119, culture designated as pVVNADL-Singp, maintained in a private repository at the campus of the University of Nebraska, in a refrigerator (Room VBS 151), in the Veterinary Basic Science Building, Department of Veterinary Science, Lincoln, Nebr. 68503 (ATCC No 97572); (2) a plasmid containing sequence-tagged genome of BVDV, strain NADL, in E. coli strain GM110, in a culture designated as pVVNADL delta Dra maintained in a private repository at the campus of the University of Nebraska, in a refrigerator (Room VBS 151), in the Veterinary Basic Science Building, Department of Veterinary Science, Lincoln, Nebr. 68503 (ATCC No. 97573); (3) a plasmid pVVNADL in a culture designated as pVVNADL maintained in a private repository at the campus of the University of Nebraska, in a refrigerator (Room VBS 151), in the Veterinary Basic Science Building, Department of Veterinary Science, Lincoln, Nebr. 68503; (4) a Chimeric BVDV, i-VVNADL-Singp, in a culture designated as i-VVNADL maintained in a private repository at the campus of the University of Nebraska, in a refrigerator (Room VBS 151), in the Veterinary Basic Science Building, Department of Veterinary Science, Lincoln, Nebr. 68503 (ATCC No. VR2529); (5) a virus i-VVNADL delta Dra in a culture designated as i-VVNADL delta Dra maintained in a private repository at the campus of the University of Nebraska, in a refrigerator (Room VBS 151), in the Veterinary Basic Science Building, Department of Veterinary Science, Lincoln, Nebr. 68503; and (6) a virus i-VVNADL in a culture designated as i-VVNADL maintained in a private repository at the campus of the University of Nebraska, in a refrigerator (Room VB5 151), in the Veterinary Basic Science Building, Department of Veterinary Science, Lincoln, Nebr. 68583.

Missing sequences were incorporated at four locations and the plasmids were joined to construct a single plasmid with the entire BVDV genome as cDNA: pVVNADL. An E. coli, strain GM119, (genotype: F-supE44 lacY1 galK2 galT22 metB1 dam-3 dcm-6 tsx-78 lambda-) was used in the preferred embodiment because of the increased plasmid stability provided by this E. coli strain. The infectious clone plasmid (pVVNADL) is not stable in some other E. coli hosts, such as MC1061, JM105, JM109, Sure, DH5a. The precise molecular basis of the increased stability in GM119 is unknown. The BVDV genome can be custom-tailored in the infectious clone plasmid pVVNADL, or one of its precursors: pBV18-F2 and p50Meu-3'. Two examples are as follows:

(a) BVDV with a unique sequence tag, i-VVNADL delta Dra, was created which is neutral with respect to phenotypic properties of BVDV; and (b) a chimeric BVDV virus, i-VVNADL Singp, which replicates like a wild-type (WT) virus in spite of the chimeric nature of its genome and its antigenic differences detected with monocolonal antibodies.

As part of this process, the 5' and 3' termini of the BVDV genome were reconstructed. This reconstruction includes the addition of BVDV genomic sequences missing or corrupted, the tailoring of signals of RNA transcription, and the engineering of cleavage sites for linearization of the DNA prior to transcription. A single nucleotide deletion present in the glycoprotein-encoding region of the virus (nt 2702) is repaired by replacement of a small fragment amplified from viral cDNA by RT-PCR. Sequence information present in all of the plasmids representing each region of the BVDV genome was verified and repaired.

Functional integrity of the T7 promotor, the 5'-UTR, and the ORF of one intermediate plasmid which encompasses the 5'-5.5 kb of the BVDV genome is verified by transfection of linearized pBV18-F2 plasmid DNA into bovine cells infected with a vaccinia virus producing T7 RNA polymerase. Because the T7 promoter in pBV18-F2 directs the synthesis of RNA transcripts representing the region of the BVDV genome encoding for the structural proteins of the virus, transfected bovine cells were probed with monoclonal antibodies (Mabs) to the viral glycoproteins. The integrity of the ORF was confirmed and it was determined that the 3' UTR of the virus is not required for translation. After this, a full-length cDNA clone, termed pVVNADL was obtained by joining a fragment of DNA derived from pBV18-F2 to plasmid P5DMeu-3'.

RNA transcripts from the full-length BVDV genome clones in pVVNADL were generated using the following procedure: DNA was linearized with SacII restriction endonuclease, which cleaves pVVNADL at the 3'-end of the BVDV genome. This DNA was used as template for in vitro transcription with T7 RNA polymerase with or without removing the 3'-overhand left by SacII. Transcription with the cap analog and transfection of the capped RNA were also tested. Production of RNA molecules identical to the BVDV genome with an exact 3' end was ascertained by gel electrophoresis and Northern Blotting. RNA synthesized in vitro was used to transfect EBTr cells by electroporation.

Controls included the electroporation of a transcription mix lacking template DNA or T7 DNA polymerase. Following electroporation, cells were distributed into dishes containing glass coverslips to allow fixation and immunofluorescence staining. Cells were monitored for possible signs of cytopathology. Monolayers on glass coverslips were fixed at 24 and 48 hours after electroporation and stained with Mab to the p80/N53 protein. Supernatant fluid from these wells was collected to check the phenotype of the rescued virus. RNA transcripts made in vitro were infectious, yielding ~$10^3 TCID_{50}/\mu g$. RNA transcribed in the presence of the cap analog had less infectivity than uncapped RNA. RNA synthesis with cap analog and reduced concentration of GTP very likely results in truncated transcripts. The phenotype of the virus rescued from pVVNADL transcripts, termed i-VVNADL, was studied in vitro.

Infectious BVDV was produced by cells transfected with uncapped RNA transcribed in vitro. The DNA template for RNA production consisted of a plasmid containing the entire genome of BVDV, cloned as cDNA. The internal ribosome entry site element in the 5'-untanslated region (UTR) of the viral genome and the functional 5'- and 3'- termini in viral genomic RNA BVDV rescued from the infectious cDNA clone had an in vitro phenotype virtually identical to the WT parent, the NADL strain of BVDV.

A genomic deletion of a single codon in the infectious clone, encoding glutamic acid at position 1600 of the viral polyprotein, gave rise to sequence tagged BVDV readily identified by restriction fragment length polymorphism analysis of reverse transcription-polymerase chain reaction (RT-PCR) amplicons. Suitability of the molecular clone of BVDV for genomic manipulations was shown by substitution of the major envelope glycoprotein E2/gp53 with that of the Singer strain, giving rise to a chimeric virus. The predicted change in antigenic structure of the chimeric virus was identified with strain-specific Mabs by neutralization or immunofluorescence assay.

Embryonic bovine trachea (EBTr) cells and the NADL strain of BVDV were obtained from the American Type Culture Collection (CCL-44 and VR-534). This strain of BVDV was isolated from the spleen of a naturally-occurring fatal case of BVDV infection.

In this process, a set of five plasmids bearing overlapping cDNAs from the BVDV genome are used to assemble a full length copy of the viral genome in a single plasmid DNA molecule, following standard procedures. These five plasmids are the five plasmids maintained in five cultures in the refrigerator (Room VB5 151) in the Veterinary Basic Science Building, Department of Veterinary Science, University of Nebraska, Lincoln, Nebr. 68583 designated as pBV18, BV116b, pBVD79, pBVF2 and pBVSD2,3.

In FIG. 1, there is shown a flow diagram of an assembly process comprising seventeen intermediate cloning steps to join the original cDNA clones, to incorporate the missing 5'- and 3'- termini of the viral genome, to restore the altered BVDV genomic sequence, as well as to tailor signals for runoff RNA transcription in vitro.

As shown in FIG. 1, five plasmids pBV-18; pBV-116P; pBVD-79; pBV-F2; and pBVSD2-3' are converted to pBV18-T7-C1aI, pBV116-C1aI, pBVDF2-79 and pBVSD-3'-M1uI as shown in step 11, 13, 15 and 17 respectively. These five intermediate plasmids are converted to the plasmid pVVNADL.

Figure 2:
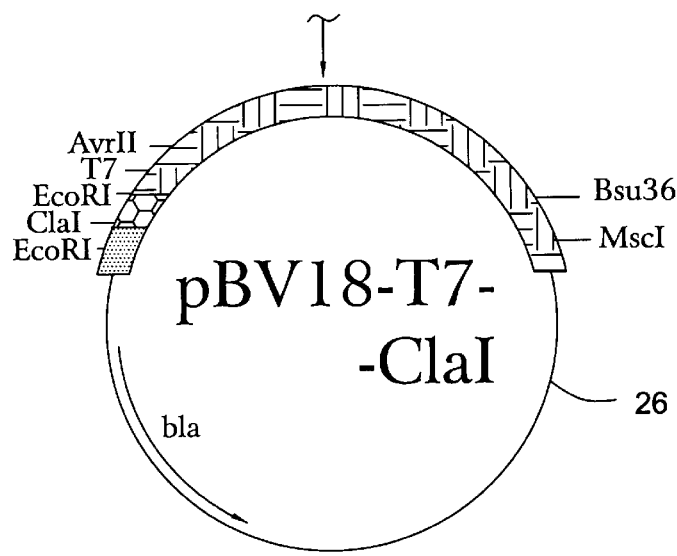
FIG. 2 is a diagram of a portion of the process of FIG. 1.

In FIG. 2, there is shown a conversion of the pBV-18 plasmid to pBV18-T7-C1aI. In this process, the plasmid 12, pBV18, has a T7 promotor and missing nt added at 5'-end terminus of the BVDV genome in step 12. A T7 synthetic promotor flanked by EcoRI AvrII restrictive site cohesive ends is ligated (covalently bonded by DNA ligase) as shown by a plasmid 22, pBV18-T7. A unique C1aI site is added by ligating a synthetic oligonucleotide part at EcoRI-C1aIEcoRI to result in a plasmid 24, pBV18-T7-C1aI. This plasmid is digested with Bsu36I and MscI to obtain a DNA fragment, labeled 26 pBV18-T7-C1aI, which will be joined to a fragment derived from PBV106-F2 (plasmid 42 in FIG. 6).

Figure 3:
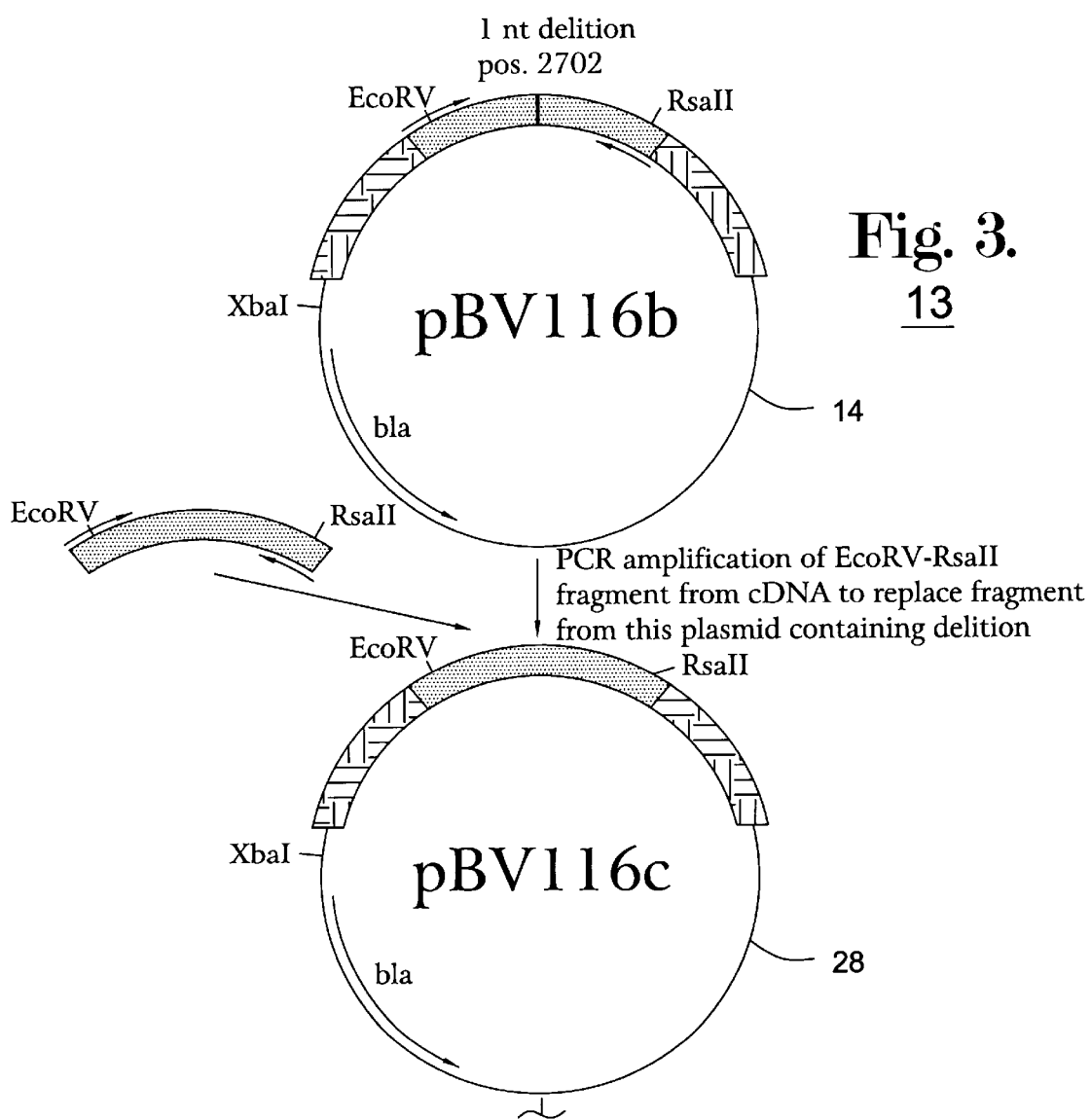
FIG. 3 is a diagram of another portion of the process of FIG. 1.
Figure 3:
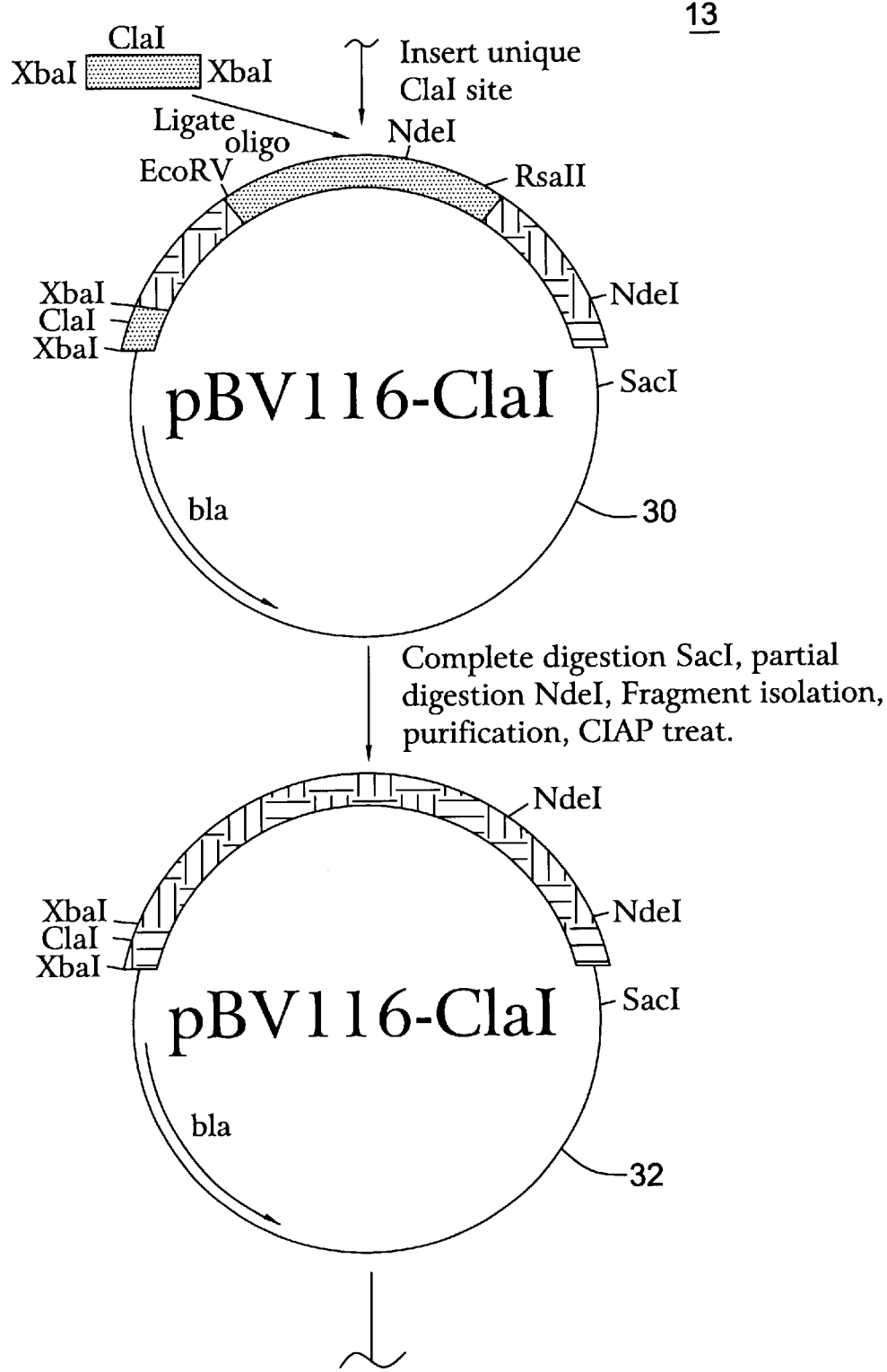

In FIG. 3, there is shown a conversion of the plasmid 14, pBV116b, to the plasmid 32, pBV116-C1aI. In this process, plasmid 14 is modified by removal of DNA fragment extracting from the ECORV site to the REC II site, followed by replacement with an analogous fragment derived from BVDV RNA by RT-PCR. The reason to replace this fragment from this plasmid was the presence of a deletion at position 2702. The result of the experiment is plasmid 28, pBV116c. The plasmid 28 has modified by the insertion of a unique C1aI site. A XbaI-C1AI- XbaI synthetic oligonucleotide pair was ligated resulting in a plasmid 30, pBV116-C1aI. The plasmid 30 is treated by complete digestion with SacI, partial digestion in NdeI, followed by fragment isolation, purification, and CIAP treatment to result in a fragment 32, a linear fragment of pBV116-C1aI.*

Figure 4:
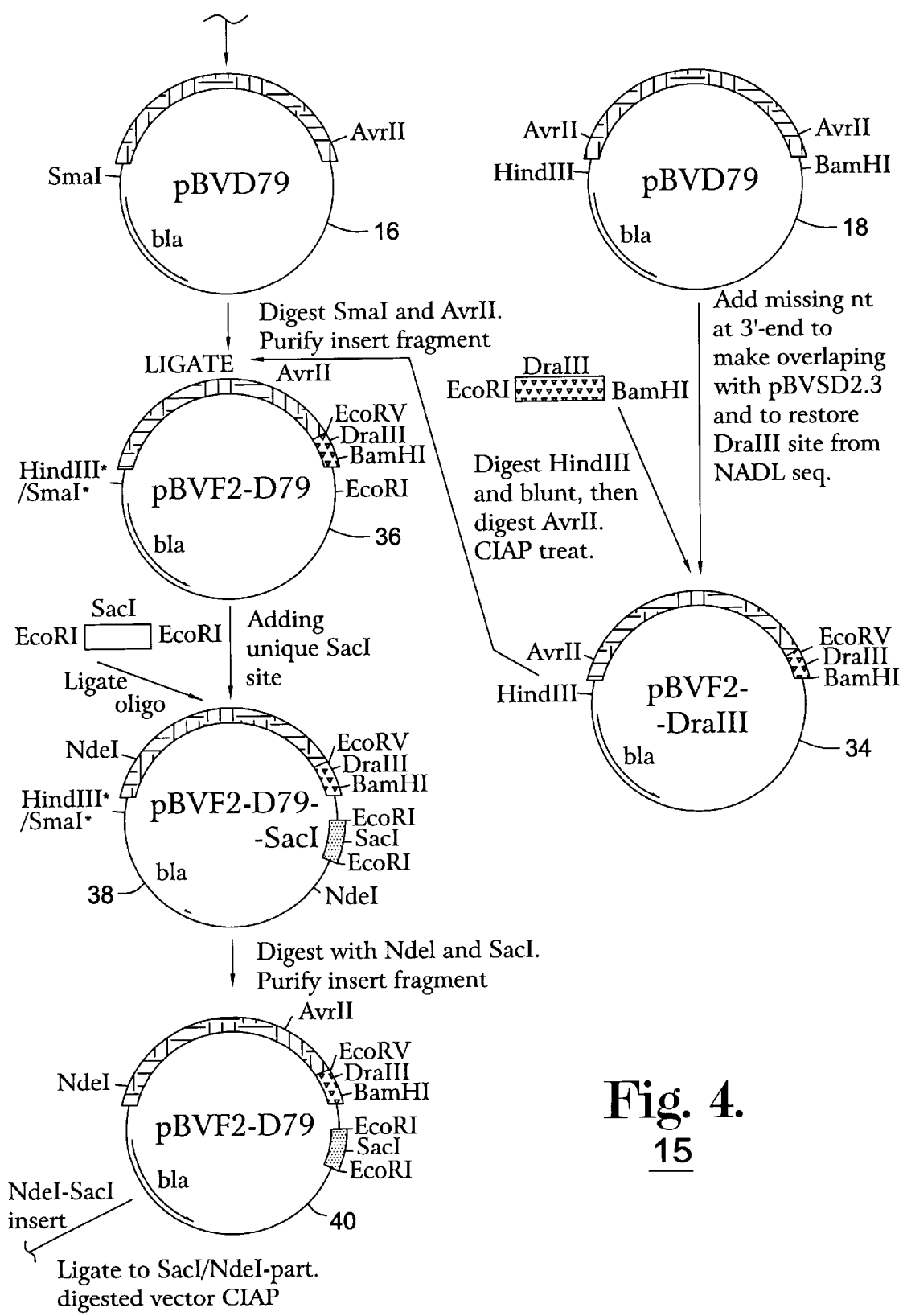
FIG. 4 is a diagram of another portion of the process of FIG. 1.
Figure 6:
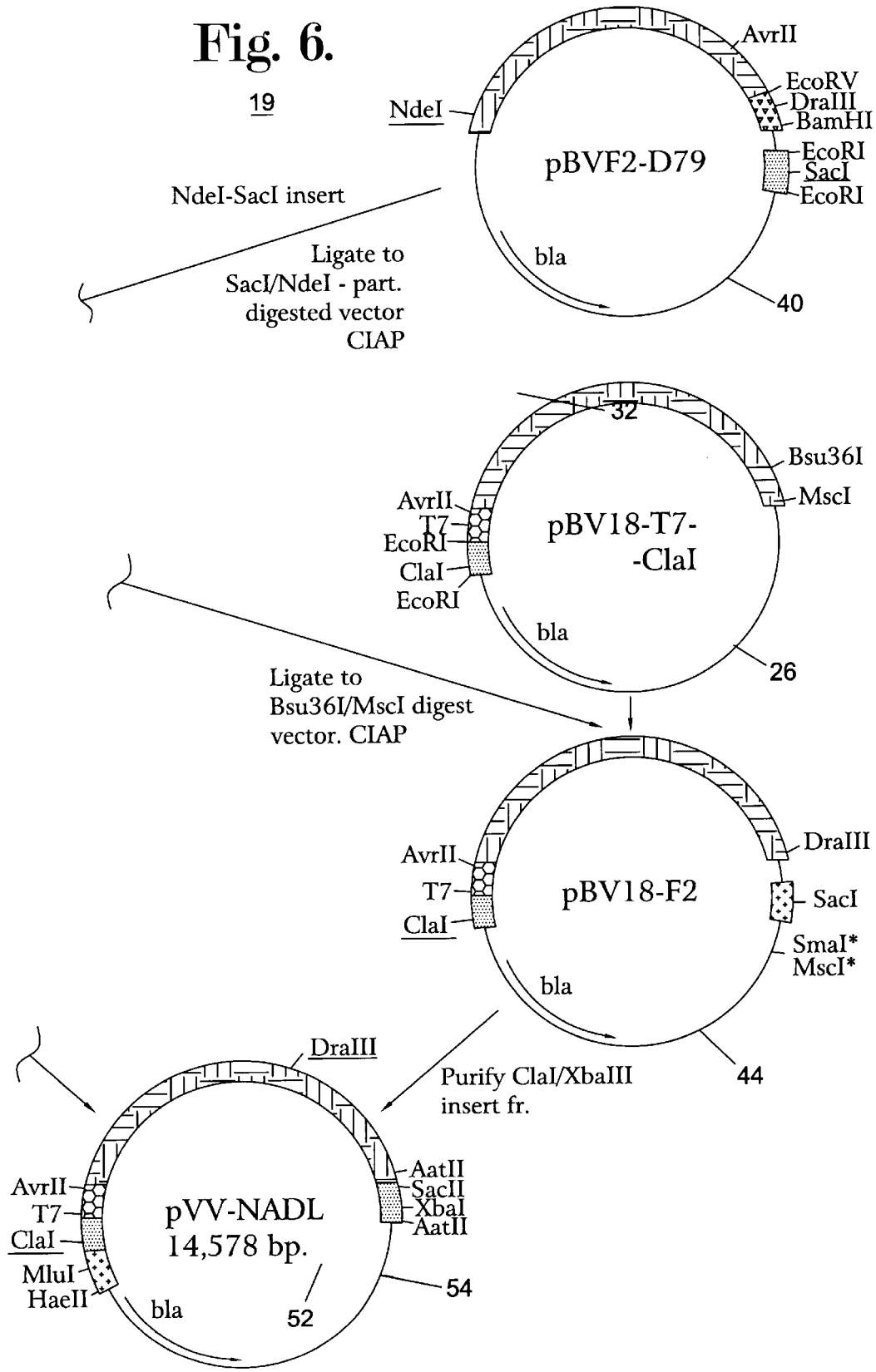
FIG. 6 is a diagram of another portion of the process of FIG. 1.
Figure 8:
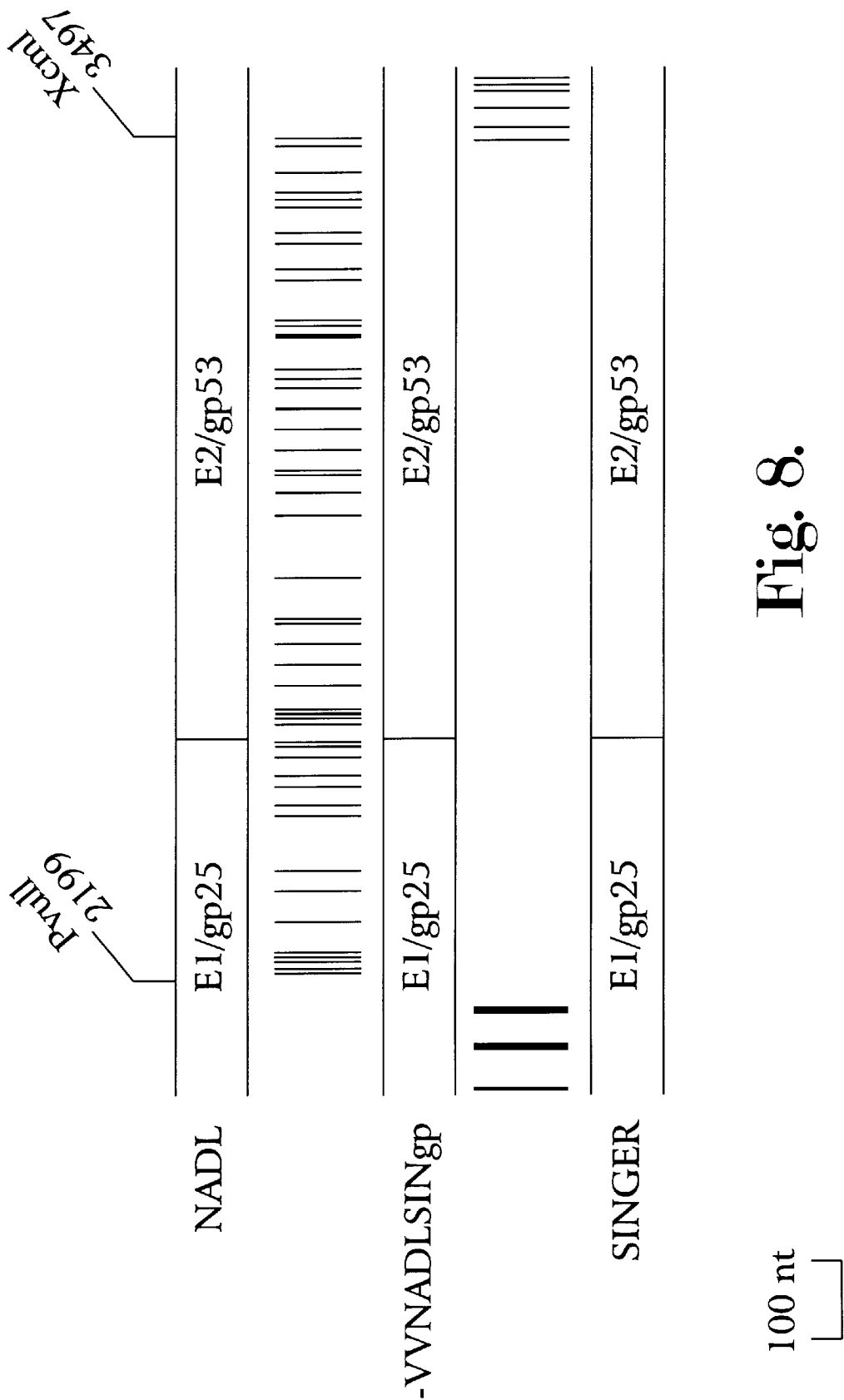
FIG. 8 is a diagram illustrating the nucleotide sequence alignment of the region of the BVDV genome between nucleotide 2040 and 3600 from 3 different viruses: the two parental and the chimeric derivative.

In FIG. 4, there is shown a conversion of the plasmid 16, pBVD79, and the plasmid 18, pBVF2, to the plasmid 40pBVF2-D79. In this process, the plasmid 18, pBVF2 is treated by adding the missing nt at 3'-end to make overlapping with pBVSD2-3' and to restore the DraIII site from the NADL by ligating oligo EcoRV-DraIII-BamHI to result in a plasmid 34, pbVf2-DraIII. A plasmid 36, pBVF2-D79, is prepared by digesting a plasmid 16, pBVD79, with SmaI and AvrII, purifying the insert fragment and with ligating into a window created in the plasmid 34, pBVF2-DraIII, by digesting with HindIII and blunting, then digesting with AvrII and followed by CIAP treatment. The plasmid 36 is treated by adding a unique SacI site. A synthetic oligonucleotide pair bearing a SacI site flanked by *E. coli* cohesive ends was ligated to form a plasmid 38, pBVF2-D79-SacI, which in turn is digested with NdeI and SacI. Purifying and inserting the fragment to result in a plasmid fragment 40, pBVF2-79. The plasmid 42 pBV116-F2, shown in FIG. 6, is prepared by combining and ligating plasmid fragment 32, shown in FIG. 3 and FIG. 6, pBV116-C1aI, modified by removal of a DNA fragment extracted from EcoRV site to the RsaII site, followed by replacement with an analogons fragment derived from BVDV RNA by RT-PCR and plasmid 40, pBVF2-D79 modified by removal of a DNA fragment extracted from EcoRV site to the RsaII site, followed by replacement with an analogons fragment derived from BVDV RNA by RT-PCR and ligating to a SacI NdeI (partly digested) vector to form the plasmid 42, pBV116-F2. A plasmid 44, pBV18-F2, is formed by combining the plasmid 26, pBV18-T7-C1aI modified by removal of a DNA fragment extracted from EcoRV site to the RsaII site, followed by replacement with an analogons fragment derived from BVDV RNA by RT-PCR, with the plasmid 42, pBV116-F2, using SmaI/Bsu36I (partly digested) ligated to Bsu36I/MscI digested vector.

Figure 5:
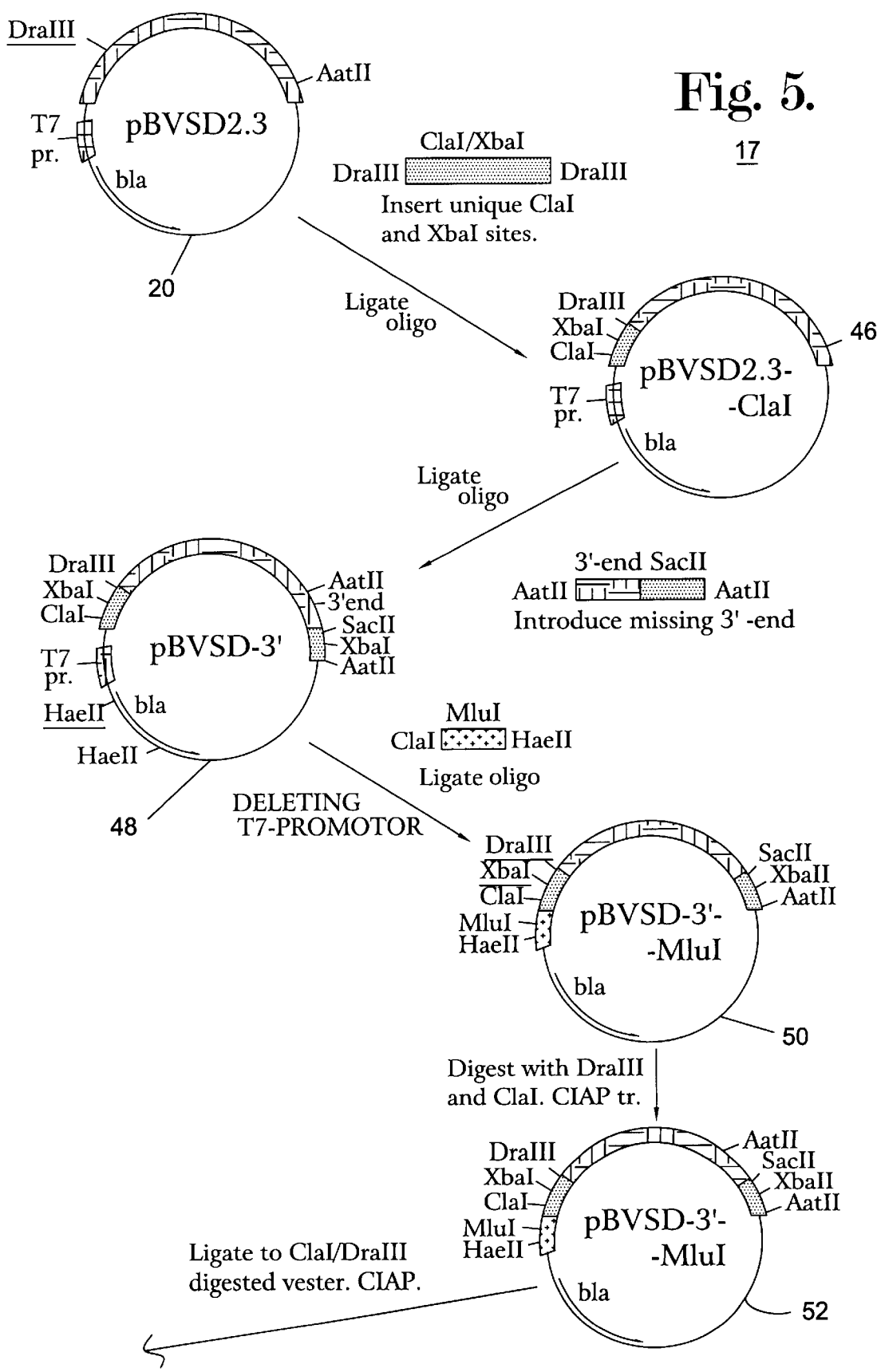
FIG. 5 is a diagram of another portion of the process of FIG. 1.

In FIG. 5, there is shown the conversion of the plasmid 20, pBVSD2-3', to the plasmid 50, pBV5D3'-MCUI. In this process, a plasmid 46, pBVSD2.3-C1aI is prepared by ligating a synthetic DraIII-C1aI/XbaI-DraIII oligonucleotide in plasmid 20, pBVSD2-3', at a unique DraIII site. The plasmid 46, pBVSD2-3'-C1aI, has the oligonucleotide AatII-3'-end SacII-AatII introduced to restore the missing sequences at the 3'-end of RIBV5V genome to form a plasmid 48, bBVSD-3'. The plasmid 48, pBVSD-3' is converted to a plasmid 50, pBVSD-3'-M1uI by deleting the T7 promotor located between the C1oI and HseII sites. A synthetic oligonucleotide linker bearing on M1uI recognition site sequence flanked by C1aI and HaeII cohesive ends was cloned at this location. The plasmid 50 pBVSD-3'-M1uI is converted to the plasmid 52, pBVSD-3'-M1uI by digesting with DraIII and C1aI, and treating with CIAP.

Finally, in FIG. 6 there is shown the conversion of the plasmid 32, pBU116-C1aI, and the plasmid 40, PBVF2-D79, to the plasmid 54, pVV-NADL, which is 14,578 bp in length. The plasmid 54 is formed by combining the plasmid 44, pBV18-F2, with the plasmid 52, pBVSD-3'-M1uI. A purified C1aI DraIII insert from plasmid 44 was ligated into the plasmid 52 previously digested with C1aI/DraIII.

The resulting plasmid, pVVNADL, consists of the full-length cDNA of the BVDV genome flanked by an upstream T7 promoter which directs the start of transcription at nucleotide position 1. A SacII recognition sequence located at the end of the BVDV 3'-UTR allows production of positive sense RNA molecules of 12578 nucleotides by runoff transcription with T7 RNA polymerase. Introduction of a sequence tag into the BVDV genome was performed by digesting pVVNADL with DraIII and treating linear DNA with T4 DNA polymerase to remove the 3'-overhang. The blunt DNA was recircularized with T4 DNA ligase and the resulting pVVNADL Dra plasmid was sequenced to verify the three-nucleotide deletion.

To substitute a region of the BVDV, NADL, genome encoding the major envelope glycoprotein, transfer vector pVVNADL delta SA was constructed deletion of a SalI-AatII fragment from pVVNADL, comprising all the nonstructural protein-encoding region downstream of the SalI site (nucleotides 5621 to 12542). A PvuII-XcmI fragment of pVVNADL SA including E2/gp53 was replaced using standard methods with a homologous cDNA fragment derived from the Singer strain of BVDV by RT-PCR. The resulting pVVNADLΔ SA-SINgp was digested with ClaI and DraIII to isolate a fragment representing the 5'-5184 nucleotides of the BVDV genome to be ligated to pSDM1u-3' digested with ClaI and DraIII to create the appropriate window. The resulting construct was designated pVVNADLSINgp and has Singer strain-derived genomic sequences from nucleotide position 2199 to 3497 replacing the original BVDV strain NADL sequences.

RNA transcripts were synthesized in vitro with T7 RNA polymerase from a template consisting of the full-length cDNA of the BVDV genome contained in pVVNADL linearized with SacII and treated with T4 to remove the 3'-overhang. The RNA was transcribed with bacteriophage T7 RNA polymerase under conditions adapted from the methods described in F. Ausubel, R. Brent, R. Kingston, J. Moore, J. Siedman, J. Smith & K. Struhl (1987) *Current Protocols in Molecular Biology* John Wiley and Sons, New York and E. T. Schenbom and R. C. Mierendorf, Jr., (1985) *Nucleic Acids Res* 13, 6223–36.

Transcription reaction products were analysed by gel electrophoresis and Northern analysis, using a probe derived from the 5'-end of the BVDV genome. RNA synthesized in vitro was digested with RNase-free DNase I, precipitated with isopropanol, washed in ethanol and used to transfect EBTr cells by electroporation as described below. Controls included the electroporation of a transcription mix lacking template DNA, or T7 RNA polymerase, or the use of a truncated subgenomic cDNA template (Sal digested). Electroporated cells were distributed into dishes containing glass coverslips to allow acetone fixation and immunostaining for fluorescence microscopy.

Integrity of the open reading frame (ORF) was assessed on Bovine Testicle (BT) cells infected with vaccinia MVA-T7 by transient transfection gene expression. Cells were fixed and probed for expression of E2/gp53 or NS23/p 125 with specific monoclonal antibodies (MAbs). RNA transfection was performed as follows:

Briefly, $3\times10^6$ EBTr cells resuspended in medium containing 3 ug isopropanol-precipitated RNA were electroporated by two consecutive discharges of 1700 V/cm and 25 uF in a 0.4 cm cuvette using a Gene Pulser instrument (Bio-Rad). RNA transfer efficiency was assessed by removing coverslips at 24 and 48 hours after plating and processing for immunofluorescence using a MAb to BVDV. Production of infectious progeny virus was assessed by harvesting culture medium from transfected monolayers, filtering through 0.45 urn membranes and inoculation onto BT cells. Infection of BT cells was monitored by development of cytopathology and immunostaining with specific Mabs. Stocks of transfection-rescued virus were prepared after three in vitro passages to be used to determine genotype and phenotype.

Phenotype analyses of all plasmid-derived viruses were carried out on stocks prepared after three cell culture passages and included plaque morphology, as well as growth kinetics analyses at three incubation temperatures, 35° C., 37° C. and 39.5° C. by standard protocols. Antigenic analyses included seroneutralization assays and immunofluorescence probing using a panel of 9 MAbs which recognize E2/gp53 polymorphisms or conserved E0/gp48 apitopes. Bovine testicle cells were infected with BVDV at an input multiplicity of five and the monolayers lysed at 18 hours after infection for RNA extraction. RT PCR was performed with appropriate synthetic oligodeoxynucleotide primer pairs. DNA amplified with Taq DNA polymerase was sequenced.

In summary, two plasmids were constructed, each carrying cDNA representing approximately the 5'- and 3'-halves of the BVDV genome. Plasmid pBV18-F2 consists of a T7 RNa polymerase promoter abutted to the viral 5'-UTR and adjacent polyprotein ORF sequences encoding the viral structural proteins. The second plasmid pBV50M1u-3' encompasses the nonstructural protein region and the 3'-UTR of the BVDV genome followed by a SacII restriction endonuclease site. These plasmids were used to join the two halves of the viral genome to give rise to a genomic-length construct termed pVVNADL.

The integrity and continuity of the polyprotein ORF was assessed by T7-driven transient expression of transfected pVVNADL DNA. Cells previously infected with vaccinia virus MVA-T7 expressing T7 RNA polymerase and transfected with pVVNADL DNA showed bright immunofluorescence following staining with Mabs to structural or nonstructural viral proteins, revealing expression of genuine BVDV proteins from an uninterrupted polyprotein ORF.

The plasmid carrying the entire genome of BVDV, pVVNADL, contains the Co1E1 replicon derived from pGEM4 and is 14,578 bases in length. The plating efficiency of *E. coli,* strain GM119 or JM109, hosts transfected with supercoiled pVVNADL DNA on ampicillin-containing solid medium is more than 100-fold lower than that of cells receiving pGEM4 DNA. *E. coli* strain GM119 proved to be a more suitable host for pVVNADL than strain JM109 which led to frequent DNA deletions.

Runoff RNa transcripts synthesized in vitro with phage T7 RNA polymerase from SacII-linearized pVVNADL were largely subgenomic in size with only a minor proportion of BVDV genome-length RNA molecules. Transfection of this unselected heterogeneous population of transcripts into EBTr cells by electroporation resulted in typical BVDV cytopathology, such as vacuolation and detachment from the matrix, after 72 hours. In contrast, EBTr cells transfected with truncated subgenomic transcripts processed in the same fashion did not show these changes. Expression of structural and nonstructural BVDV proteins was observed in 1–3% of the EBTr cell population as early as 24 hours after transfection by immunofluorescence with BVDV-specific MAbs. The proportion of positive cells rose to 10–20 percent by 48 hours following transfection.

Cell culture fluids were harvested periodically and used for the propagation of the rescued infectious virus on bovine testicle (BT) cells to carry out genetic and phenotypic characterization. Culture supernatants from EBTr cells transfected with pVVNADL-templated transcripts caused cytopathic changes in bovine testicle BT cells 48 hours after inoculation, while cell culture medium from control EBTr monolayers transfected with truncated transcripts had no effect. The antigenic phenotype of the virus rescued from pVVNADL transcripts, termed i-VVNADL, was identical to the parental NADL virus by immunofluorescence straining with a panel of Mabs against the E2/gp53 envelope glycoprotein and E0/gp48.

Growth parameters of the i-VVNADL at different temperatures were indistinguishable from parental BVDV NADL virus by plaque morphology and kinetics of growth determined at 35° C., 37° C., and 39.5° C. Thus, BVDV rescued from pVVNADL is essentially identical to the parental NADL strain of BVDV in vitro. Genetic manipulations of the NADL strain of BVDV involving the creation of BVDV cDNA plasmid intermediates propagated in *E. coli* does not alter the in vitro phenotype of the resulting i-VVNADL.

The introduction of a sequence tag into the BVDV genome allows unambiguous identification of the viruses rescued from plasmid-derived RNA transcripts and facilitates the interpretation of experimental data. The model tag should ideally be a unique sequence, readily identifiable by restriction fragment length polymorphism analysis and be neutral with respect to the viral phenotype. A deletion was introduced in the pVVNADL infectious clone which results in loss of a DraIII restriction enzyme recognition site and gain of a PmlI recognition site.

An infectious virus was rescued from pVVNALDL Dra-templated transcripts with the same kinetics as with the intact WT cDNA infectious clone, the transfected cells showed a large proportion of infected cells by immunofluorescence of coverslips fixed at 48 hours. Characteristic vacuolating cytopathology could be observed in transfected cells between 72–96 hours after transfection and in subsequent passages of the culture medium onto new BT cells.

Restriction enzyme analysis of a 183 base pair amplicon spanning the DraIII site amplified by RT-PCR from i-VVNADL Dra revealed the presence of a PmlI site (CACGTG) and the absence of a Dram site (CACagaGTG). In contrast, DNA amplified from parental virus showed the reciprocal susceptibility to cleavage with these enzymes, characteristic of the NADL strain of BVDV. Antigenic analysis reveals that the i-VVNADL Dra virus is essentially identical to the parental NADL virus as ascertained by MAb analyses. Growth properties of i-VVNADL Dra analyzed in vitro were similar to those of WT. Thus, the single amino acid deleted from the vicinity of the putative cleavage site within p125/NS23 did not affect its viability and phenotype in vitro.

Reverse genetic approaches may be used to construct chimeras of viral genomic RNA for identification of genomic sequences responsible for a given phenotypic character. Antigenic chimeras of BVDV prototype NADL strain with the widely used strain Singer were constructed for this purpose. Unique markers are present exclusively in each of the two parental strains and were used to identify the newly created chimeric virus only if it carried both markers. One marker, a unique 270 base stretch of sequence derived from the cattle genome at position 4993, is characteristic of the NADL strain of BVDV. The other marker consisted of unique amino acid sequences of the E2/gp53 envelope glycoprotein which confer the Singer strain reactivity with Mabs 20, 31, 32, and 39 by immunoassay and neutralization. Thus, the Singer strain does not have the 270 nucleotide insert while the NADL strain fails to react with the selected set of four MAbs.

By replacing the original envelope glycoprotein in the WT infectious clone with sequences coding for the Singer envelope genes, a chimeric virus which will carry the epitopes present in the Singer strain envelope and the 270 nucleotide bovine insert at position 4993 is obtained. The pVVNADL PvuII-XcmI fragment (position 2199 to 3497) which encodes for the C-terminus of E1/gp25 and the entire ectodomain of E2/gp53 was substituted with homologous sequences from the Singer strain of BVDV giving rise to plasmid pVVNADLSINgp. An infectious chimeric BVOV was recovered from transcripts derived from pVVNADLS-INgp. Plaque morphology and growth kinetics of the chimeric virus, termed i-VVNADLSINgp, revealed that its growth properties are virtually identical to its parental NADL strain virus. By contrast, the antigenic properties of the chimeric virus depart from the BVDV strain NADL ancestor. The pattern of reactivity of proteins encoded by i-NADLSINgp with a panel of E2/gp53 with an antigenic profile identical to the Singer isolate by immunofluorescence. Subtle differences were observed between these viruses in neutralization titers with Mabs 10 and 39, but the overall patterns remained the same.

The virus recovered from the parental pVVNADL cDNA has a gp53 indistinguishable from that of the NADL strain. Nucleotide sequence analyses of the i-VVNADLSINgp chimeric virus genomic RNA across the substituted fragment and the flanking regions reveals the chimeric structure of the genome. Furthermore, the 270 nucleotide bovine sequence insert at nucleotide 4993 characteristic of the NADL strain is present in i-VVNADLSINgp chimeric virus genomic RNA, as indicated by the size of the amplicon obtained by RT-PCR. Thus, the experimental evidence indicates that i-VVNADLSINgp represents a chimeric virus consisting of a genomic backbone from NADL strain of BVDV, but expressing the Singer strain E2/gp53 glycoprotein as well as the C-terminal end of E1/gp25.

The simple observation that uncapped RNA transcripts produced by T7 RNA polymerase from pVVNADL template establishes three concepts. The first concerns the structure of the 5'- end of the viral RNA. RNA without a 5'-cap structure was infectious, suggesting that a cap-independent translation initiation mechanism is used by BVDV genomic RNA for gene expression. This result is compatible with biochemical evidence suggesting that the 5'- end of genomic RNA was not blocked by inverted methylguanosine. The second concept emerges as a corollary of the first. An internal ribosome entry site element in the 5'-UTR of the BVDV genome identified in reticulocyte lysates must be functional during virus infection of cells. The third concept relates to the sequences of the extreme 5'- and 3'- temini of the viral RNA, thought to contain minus and plus strand RNA replicase promoter elements, respectively. Technical difficulties are commonly encountered in approaches to determine the 5'- and 3'- termini of large viral RNA molecules. However, the sequences reported by Deng and Brock, "5' and 3' Untranslated Regions of Pestivirus Genome: Primary and Secondary Structure Analyses," *Nucleic Acids Research,* 1993, Vol 21, No. 8, 1949–1957, and incorporated in pVVNADL gave rise to infectious virus with WT phenotype, indicating their functionality for the first time.

The 12,578 bases long genome of BVDV constitutes one of the largest known positive strand viral cDNA clone which yields infectious RNA transcripts. Moreover, the cDNA clone is replicated as a single plasmid in *E. coli*. The plating efficiency of *E. coli* hosts, such as strain JM109, transformed with pVVNADL and its derivatives and plated on ampicillin selective medium was reduced by at least 2 orders of magnitude as compared to the pGEM4 vector alone. In addition, a high frequency of deletions in transformant strain JM109 *E. coli* was observed. Instability of large cDNA clones is not uncommon and often determines utilization of alternative strategies involving generation of transcription DNA templates in vitro by ligation or long PCR. However, we found that certain strains of *E. coli,* notably GM119, circumvented such difficulties. The basis or biochemical correlates of the greater stability of pVVNADL in this host are unknown.

Full-length runoff transcripts were produced in vitro with low efficiencies by T7 RNA polymerase, apparently due to the intrinsic properties of the 12.5 kB pVVNADL template. Although the T7 RNA polymerase is highly processive for elongation of shorter transcripts, certain secondary structures in nascent transcripts can act as termination signals. The probability of such fortuitous events increases with transcript length. The presence of discrete subgenomic length RNA molecules was sometimes observed in electropherograms of transcription reaction products. Low yields of full-length transcripts are not uncommon and also occur in other pestivirus cDNAs as shown for hog cholera virus in two independent reports. Unfractionated transcription products yielded infectious viruses readily upon transfection. Because only a relatively minor population of transcripts is full-length, it is likely to have a high specific infectivity. Others have reported considerably longer delays before an infectious virus is recovered from transfected monolayers.

The in vitro phenotype of the virus rescued from the pVVNADL as defined by the parameters and characteristics studied did not depart significantly from those of the parental BVDV strain NADL. Interestingly, shuttling of the large BVDV RNA genome through cDNA in a prokaryotic plasmid did not result in changes of the viral phenotype in vitro. Animal inoculation studies will be required to determine if the same is true of the in vitro phenotype of i-VVNADL. The wild-type nature of the virus rescued from pVVNADL makes it an ideal backbone to engineer changes leading to attenuation by reverse genetic approaches.

The high plasticity that characterizes RNA genomes makes it useful to design genomic tags that consist of more than single nucleotide changes to avoid reversion. However, large insertions or deletions may result in major decreases in replication fitness, favoring emergence of genomes repaired by RNA recombination. A deletion of three nucleotides (5182–5184: codon 1600) within the 270 nucleotide insert present in the NS23 coding region of the genome was used. Presence of this bovine sequence element at nucleotide 4993 is correlated with proteolytic processing of NS23, and the latter coincides with viral cytopathogenicity and virulence.

Infection of BT cells with the tagged i-VVNADL Dra virus resulted in cell death with the same kinetics and features of the parental strain. Thus, glutamic acid at position 1600 in the NADL strain polyprotein is not important for viral cytopathogenicity. However, this deletion resulted in a convenient restriction fragment length polymorphism tag providing a convenient means to discriminate between WT and tagged genomes. Although the virulence of this virus in cattle has not been determined experimentally (observed), its in vitro properties are identical to the WT. Therefore, i- VVNADL Dra constitutes a good candidate virus with a neutral genomic tag to further examine BVDV pathogenicity.

The glycoprotein chimera of BVDV displays a unique antigenic phenotype without alterations in replication properties in vitro. This virus can simply be traced using two markers: the unique epitopes present in E2/gp53 of the Singer strain of BVDV detected with specific Mabs (e.g. 10f9) and the presence of a unique 270 base pair bovine sequence insert after nucleotide 4993, detected by PCR, characteristic of the NADL parent and absent in the Singer genome.

Neutralization of virus infectivity by Mabs results from a high-affinity interaction between glycoprotein and antibody (Ka values between $10^8$ and $10^{10}$ 1.mol$^{-1}$). Even minor conformational changes in the viral glycoprotein can lower the affinity of the interaction ($10^6$ to $10^7$ 1.m01$^{-1}$) and impair neutralization without preventing binding in immunoassays. Mabs 10 and 39 neutralized the chimeric virus to a lesser extent as compared to the WT BVDV Singer, suggesting extramolecular influences on the interaction between the Mab IgG and E2/gp53. For example, the structure of the E2/gp53 may be affected by association with a different E1/gp25 heterodimer partner in i-VVNADLSINgp leading to a decreased interaction affinity. Mabs 10 and 39 reacted with the chimeric virus in immunofluorescence assays, in accordance with the well established lower stringency of this assay.

Reverse genetics approaches can be used to introduce specific alterations or tags into the BVDV genome, as exemplified by the deletion of codon position 1600 (glutamic acid). Moreover, construction of chimeric virus is also feasible, as evidence by the expression of an envelope glycoprotein from a different BVDV strain. The two main approaches to explore gene function in positive strand RNA virus can now be implemented using infectious cDNA clones of BVDV.

Although the upper size limits of viable BVDV genomes are unknown, at least 2 KB of additional coding sequences can be part of viable virus. Consequently, it may be possible to use BVDV as a vector to express foreign proteins for immunization purposes. It will be of interest to determine if interspecies chimeras with other pestivirus or hepatitis C and G virus are viable. Precedents exist in picornavirus and flavivirus supporting the notion that different viral functional units can be substituted with those of distantly related virus. Notably, the hepatitis C internal ribosome entry site element is functional in poliovirus-hepatitis C chimeras (56). These chimeric approaches could lead to understanding of in vitro host range in pestivirus and hepatitis C virus. Finally, infectious clones could be used to engineer attenuating mutations leading to development of novel live vaccines.

Although a preferred embodiment of the invention has been described with some particularity, many modifications and variations of the preferred embodiment are possible in the light of the above teachings. It is to be understood that, within the scope of the appended claims, the invention can be practiced other than as specifically described.

The following is claimed:

1. A method of producing recombinantly engineered infectious bovine viral diarrhea virus comprising:
   providing a vector comprising a reverse transcribed copy of bovine viral diarrhea virus RNA;
   recombinantly engineering the reverse transcribed copy of the bovine viral diarrhea virus;
   transforming an *E. coli* with the vector;
   causing the transformed host cell to produce a plurality of vectors;
   extracting the plurality of vectors from the transformed host cell;
   forming a plurality of synthesized RNA from the plurality of vectors comprising the reverse transcribed copy of the bovine viral diarrhea virus RNA;
   introducing the synthesized RNA into a mammalian cell; and
   recovering the recombinantly engineered infectious bovine viral diarrhea virus from the mammalian cell.

2. The method of claim 1 wherein the *E. coli* is strain GM119.

3. The method of claim 1 wherein the step of introducing the bovine viral diarrhea virus RNA into the mammalian cell utilizes electroporation.

4. The method of claim 1 wherein the mammalian cell is an embryonic bovine tracheal cell.

5. The method of claim 1 wherein the vector comprises pVVNADL-SINgp.

6. The method of claim 1 wherein the vector contains a selective marker for transformed cells.

7. The method of claim 1 wherein the vector comprises pVVNADLΔDra.

8. A method of producing recombinantly engineered infectious bovine viral diarrhea virus comprising:
   providing a vector comprising a reverse transcribed copy of bovine viral diarrhea virus RNA;
   recombinantly engineering the reverse transcribed copy of the bovine viral diarrhea virus to form a recombinantly engineered vector;
   transforming *E. coli*, strain GM119, with the recombinantly engineered vector;
   causing the transformed *E. coli* to produce a plurality of the recombinantly engineered vectors;
   extracting the plurality of recombinantly engineered vectors from the transformed *E. coli*;
   forming a plurality of synthesized RNA from the plurality of recombinantly engineered vectors comprising the reverse transcribed copy of bovine viral diarrhea virus RNA;
   introducing the synthesized RNA into an embryonic bovine tracheal cell by electroporation; and
   recovering the recombinantly engineered infectious bovine viral diarrhea virus.

9. A method of isolating a plurality of recombinantly engineered bovine viral diarrhea virus comprising:
   providing a vector comprising a reverse transcribed copy of a genome of bovine viral diarrhea virus RNA;
   creating a recombinantly engineered infectious bovine viral diarrhea virus;
   causing a host cell to produce a plurality of recombinantly engineered infectious bovine viral diarrhea virus; and
   isolating the plurality of recombinantly engineered bovine viral diarrhea virus.

10. A method of producing recombinantly engineered infectious bovine viral diarrhea virus comprising:
    providing a pVVNADL;
    recombinantly engineering pVVNADL to form a recombinantly engineered pVVNADL;
    transforming *E. coli*, strain GM119, with the recombinantly engineered pVVNADL to form a transformed *E. coli*;
    causing the transformed *E. coli* to produce a plurality of the recombinantly engineered pVVNADL;
    extracting the plurality of recombinantly engineered pVVNADL from the transformed *E. coli*;
    forming a plurality of synthesized RNA from the plurality of recombinantly engineered pVVNADL;
    introducing the plurality of synthesized RNA into an embryonic bovine tracheal cell by electroporation; and
    recovering the recombinantly engineered infectious bovine viral diarrhea virus.

11. An isolated vector adapted to produce recombinantly engineered infectious bovine viral diarrhea virus.

12. The vector of claim 11, further comprising a sequence tag.

13. A chimeric vector comprising a 270 nucleotide insert and an envelope glycoprotein from Singer strain bovine viral diarrhea virus wherein the vector is adapted to produce a chimeric infectious bovine viral diarrhea virus.

14. The vector of claim 13 wherein the vector comprises pVVNADL-SINgp.

15. The vector of claim 13, wherein the synthesized RNA is introduced into EBTr cells.

16. An isolated vector comprising sequence ID. NO. 1.

17. A vector comprising pVVNADL-SINgp.

18. A vector comprising pVVNADLΔDra.

19. A chimeric virus comprising i-VVNADL-SINgp.

20. A recombinant bovine viral diarrhea virus comprising i-VVNADLΔDra.

21. A plurality of recombinantly engineered infectious bovine viral diarrhea virus produced by the process comprising:
    providing a vector comprising a reverse transcribed copy of a genome of bovine viral diarrhea virus RNA;
    creating a recombinantly engineered infectious bovine viral diarrhea virus;
    causing a host cell to produce a plurality of recombinantly engineered infectious bovine viral diarrhea virus; and
    isolating the plurality of recombinantly engineered infectious bovine viral diarrhea virus.

* * * * *

SEQUENCE LISTING

<160> NUMBER OF SEQ ID NOS: 1

<210> SEQ ID NO 1
<211> LENGTH: 14578
<212> TYPE: DNA
<213> ORGANISM: bovine viral diarrhea virus

<400> SEQUENCE: 1
cacgcgtatc gatgaattcg ttaatacgac tcactatagt atacgagaat tagaaaaggc      60
actcgtatac gtattgggca attaaaaata ataattaggc ctagggaaca aatccctctc     120
agcgaaggcc gaaaagaggc tagccatgcc cttagtagga ctagcataat gagggggta     180

-continued

```
gcaacagtgg tgagttcgtt ggatggctta agccctgagt acagggtagt cgtcagtggt    240
tcgacgcctt ggaataaagg tctcgagatg ccacgtggac gagggcatgc ccaaagcaca    300
tcttaacctg agcggggtc gcccaggtaa aagcagtttt aaccgactgt tacgaataca     360
gcctgatagg gtgctgcaga ggcccactgt attgctacta aaatctctg ctgtacatgg     420 cacatggagt tgatcacaaa tgaacttta tacaaaacat acaaacaaaa acccgtcggg     480
gtggaggaac ctgtttatga tcaggcaggt gatcccttat ttggtgaaag gggagcagtc    540
caccctcaat cgacgctaaa gctcccacac aagagagggg aacgcgatgt tccaaccaac    600
ttggcatcct taccaaaaag aggtgactgc aggtcgggta atagcagagg acctgtgagc    660
gggatctacc tgaagccagg gccactattt taccaggact ataaaggtcc cgtctatcac    720
agggccccgc tggagctctt tgaggaggga tccatgtgtg aaacgactaa acggatagggg   780 agagtaactg gaagtgacgg aaagctgtac cacatttatg tgtgtataga tggatgtata    840
ataataaaaa gtgccacgag aagttaccaa agggtgttca ggtgggtcca taataggctt    900
gactgccctc tatgggtcac aagttgctca gacacgaaag aagagggagc aacaaaaaag    960
aaaacacaga aacccgacag actagaaagg gggaaaatga aaatagtgcc caagaatct   1020 gaaaaagaca gcaaaactaa acctccggat gctacaatag tggtggaagg agtcaaatac   1080
caggtgagga agaagggaaa accaagagt aaaaacactc aggacggctt gtaccataac    1140
aaaaacaaac ctcaggaatc acgcaagaaa ctggaaaaag cattgttggc gtgggcaata   1200
atagctatag ttttgtttca agttacaatg ggagaaaaca taacacagtg gaacctacaa   1260
gataatggga cggaagggat acaacgggca atgttccaaa gggtgtgaa tagaagttta   1320 catggaatct ggccagagaa aatctgtact ggcgtcccctt cccatctagc caccgatata   1380
gaactaaaaa caattcatgg tatgatggat gcaagtgaga agaccaacta cacgtgttgc   1440
agacttcaac gccatgagtg gaacaagcat ggttggtgca actggtacaa tattgaaccc   1500
tggattctag tcatgaatag aacccaagcc aatctcactg agggacaacc accaagggag   1560
tgcgcagtca cttgtaggta tgatagggct agtgacttaa acgtggtaac acaagctaga   1620
gatagcccca cacccttaac aggttgcaag aaaggaaaga acttctcctt tgcaggcata   1680
ttgatgcggg gcccctgcaa ctttgaaata gctgcaagtg atgtattata caagaacat   1740 gaacgcatta gtatgttaca ggatctaact ctttaccttg ttgacgggtt gaccaactcc   1800
ttagaaggtg ccagacaagg aaccgctaaa ctgacaacct ggttaggcaa gcagctcggg   1860
atactaggaa aaagttgga aaacaagagt aagacgtggt ttggagcata cgctgcttcc   1920
ccttactgtg atgtcgatcg caaaattggc tacatatggt atacaaaaaa ttgcaccct    1980 gcctgcttac ccaagaacac aaaaattgtc ggccctggga aatttgacac caatgcagag   2040
gacggcaaga tattacatga tgggggggt cacttgtcgg aggtactact actttctta    2100 gtggtgctgt ccgacttcgc accggaaaca gctagtgtaa tgtacctaat cctacatttt   2160
tccatcccac aaagtcacgt tgatgtaatg gattgtgata agaccccagtt gaacctcaca   2220 gtggagctga caacagctga agtaatacct gggtcggtct ggaatctagg caaatatgta   2280
tgtataagac caaattggtg gccttatgag acaactgtag tgttggcatt tgaagaggtg   2340
agccaggtgg tgaagttagt gttgagggca ctcagagatt taacacgcat ttggaacgct   2400
gcaacaacta ctgctttttt agtatgcctt gttaagatag tcaggggcca gatggtacag   2460
ggcattctgt ggctactatt gataacaggg gtacaagggc acttggattg caaacctgaa   2520
ttctcgtatg ccatagcaaa ggacgaaaga attggtcaac tgggggctga aggccttacc   2580
```

-continued

```
accacttgga aggaatactc acctggaatg aagctggaag acacaatggt cattgcttgg    2640
tgcgaagatg ggaagttaat gtacctccaa agatgcacga gagaaaccag atatctcgca    2700
atcttgcata caagagcctt gccgaccagt gtggtattca aaaaactctt tgatgggcga    2760
aagcaagagg atgtagtcga aatgaacgac aactttgaat ttggactctg cccatgtgat    2820
gccaaaccca tagtaagagg gaagttcaat acaacgctgc tgaacggacc ggccttccag    2880
atggtatgcc ccataggatg gacagggact gtaagctgta cgtcattcaa tatggacacc    2940
ttagccacaa ctgtggtacg gacatataga aggtctaaac cattccctca taggcaaggc    3000
tgtatcaccc aaaagaatct gggggaggat ctccataact gcatccttgg aggaaattgg    3060
acttgtgtgc ctggagacca actactatac aaagggggct ctattgaatc ttgcaagtgg    3120
tgtggctatc aatttaaaga gagtgaggga ctaccacact accccattgg caagtgtaaa    3180
ttggagaacg agactggtta caggctagta gacagtacct cttgcaatag agaaggtgtg    3240
gccatagtac cacaagggac attaaagtgc aagataggaa aaacaactgt acaggtcata    3300
gctatggata ccaaactcgg acctatgcct tgcagaccat atgaaatcat atcaagtgag    3360
gggcctgtag aaaagacagc gtgtactttc aactacacta agacattaaa aaataagtat    3420
tttgagccca gagacagcta ctttcagcaa tacatgctaa aaggagagta tcaatactgg    3480
tttgacctgg aggtgactga ccatcaccgg gattacttcg ctgagtccat attagtggtg    3540
gtagtagccc tcttgggtgg cagatatgta ctttggttac tggttacata catggtctta    3600
tcagaacaga aggccttagg gattcagtat ggatcagggg aagtggtgat gatgggcaac    3660
ttgctaaccc ataacaatat tgaagtggtg acatacttct tgctgctgta cctactgctg    3720
agggaggaga gcgtaaagaa gtgggtctta ctcttatacc acatcttagt ggtacaccca    3780
atcaaatctg taattgtgat cctactgatg attgggggatg tggtaaaggc cgattcaggg    3840
ggccaagagt acttggggaa aatagacctc tgttttacaa cagtagtact aatcgtcata    3900
ggtttaatca tagctaggcg tgacccaact atagtgccac tggtaacaat aatggcagca    3960
ctgagggtca ctgaactgac ccaccagcct ggagttgaca tcgctgtggc ggtcatgact    4020
ataaccctac tgatggttag ctatgtgaca gattatttta gatataaaaa atggttacag    4080
tgcattctca gcctggtatc tgcggtgttc ttgataagaa gcctaatata cctaggtaga    4140
atcgagatgc cagaggtaac tatcccaaac tggagaccac taactttaat actattatat    4200
ttgatctcaa caacaattgt aacgaggtgg aaggttgacg tggctggcct attgttgcaa    4260
tgtgtgccta tcttattgct ggtcacaacc ttgtgggccg acttcttaac cctaatactg    4320
atcctgccta cctatgaatt ggttaaatta tactatctga aaactgttag gactgataca    4380
gaaagaagtt ggctaggggg gatagactat acaagagttg actccatcta cgacgttgat    4440
gagagtggag agggcgtata tctttttcca tcaaggcaga agcacaggg gaattttttct    4500 atactcttgc cccttatcaa agcaacactg ataagttgcg tcagcagtaa atggcagcta    4560
atatacatga gttacttaac tttggacttt atgtactaca tgcacaggaa agttatagaa    4620
gagatctcag gaggtaccaa cataatatcc aggttagtgg cagcactcat agagctgaac    4680
tggtccatga agaagaggga gagcaaaggc ttaaagaagt tttatctatt gtctggaagg    4740
ttgagaaacc taataataaa acataaggta aggaatgaga ccgtggcttc ttggtacggg    4800
gaggaggaag tctacggtat gccaaagatc atgactataa tcaaggccag tacactgagt    4860
aagagcaggc actgcataat atgcactgta tgtgagggcc gagagtggaa aggtggcacc    4920
tgcccaaaat gtggacgcca tgggaagccg ataacgtgtg ggatgtcgct agcagatttt    4980
```

-continued

```
gaagaaagac actataaaag aatctttata agggaaggca actttgaggg tatgtgcagc    5040
cgatgccagg gaaagcatag gaggtttgaa atggaccggg aacctaagag tgccagatac    5100
tgtgctgagt gtaataggct gcatcctgct gaggaaggtg acttttgggc agagtcgagc    5160
atgttgggcc tcaaaatcac ctactttgcg ctgatggatg gaaaggtgta tgatatcaca    5220
gagtgggctg gatgccagcg tgtgggaatc tccccagata cccacagagt cccttgtcac    5280
atctcatttg gttcacggat gcctttcagg caggaataca atggctttgt acaatatacc    5340 gctaggggc aactatttct gagaaacttg cccgtactgg caactaaagt aaaaatgctc     5400
atggtaggca accttggaga agaaattggt aatctggaac atcttgggtg gatcctaagg    5460
gggcctgccg tgtgtaagaa gatcacagag cacgaaaaat gccacattaa tatactggat    5520
aaactaaccg cattttttcgg gatcatgcca agggggacta cacccagagc cccggtgagg   5580
ttccctacga gcttactaaa agtgaggagg ggtctggaga ctgcctgggc ttacacacac    5640
caaggcggga taagttcagt cgaccatgta accgccggaa aagatctact ggtctgtgac    5700
agcatgggac gaactagagt ggtttgccaa agcaacaaca ggttgaccga tgagacagag    5760
tatggcgtca agactgactc agggtgccca gacggtgcca gatgttatgt gttaaatcca    5820
gaggccgtta acatatcagg atccaaaggg gcagtcgttc acctccaaaa gacaggtgga    5880
gaattcacgt gtgtcaccgc atcaggcaca ccggctttct tcgacctaaa aaacttgaaa    5940
ggatggtcag gcttgcctat atttgaagcc tccagcggga gggtggttgg cagagtcaaa    6000
gtagggaaga atgaagagtc taaacctaca aaaataatga gtggaatcca gaccgtctca    6060
aaaaacagag cagacctgac cgagatggtc aagaagataa ccagcatgaa caggggagac    6120
ttcaagcaga ttactttggc aacagggcca ggcaaaacca cagaactccc aaaagcagtt    6180
atagaggaga taggaagaca caagagagta ttagttctta taccattaag ggcagcggca    6240
gagtcagtct accagtatat gagattgaaa cacccaagca tctctttaa cctaaggata    6300 ggggacatga aagaggggga catggcaacc gggataacct atgcatcata cgggtacttc    6360
tgccaaatgc ctcaaccaaa gctcagagct gctatggtag aatactcata catattctta    6420
gatgaatacc attgtgccac tcctgaacaa ctggcaatta tcgggaagat ccacagattt    6480
tcagagagta taagggttgt cgccatgact gccacgccag cagggtcggt gaccacaaca    6540
ggtcaaaagc acccaataga ggaattcata gcccccgagg taatgaaagg ggaggatctt    6600
ggtagtcagt tccttgatat agcagggtta aaaataccag tggatgagat gaaaggcaat    6660
atgttggttt ttgtaccaac gagaaacatg gcagtagagg tagcaaagaa gctaaaagct    6720
aagggctata actctggata ctattacagt ggagaggatc cagccaatct gagagttgtg    6780
acatcacaat cccctatgt aatcgtggct acaaatgcta ttgaatcagg agtgacacta    6840
ccagatttgg acacggttat agacacgggg ttgaaatgtg aaaagagggt gagggtatca    6900
tcaaagatac ccttcatcgt aacaggcctt aagaggatgg ccgtgactgt gggtgagcag    6960
gcgcagcgta ggggcagagt aggtagagtg aaacccggga ggtattatag gagccaggaa    7020
acagcaacag ggtcaaagga ctaccactat gacctcttgc aggcacaaag atacggatt    7080 gaggatggaa tcaacgtgac gaaatccttt agggagatga attacgattg gagcctatac    7140
gaggaggaca gcctactaat aacccagctg gaaatactaa ataatctact catctcagaa    7200
gacttgccag ccgctgttaa gaacataatg gccaggactg atcacccaga gccaatccaa    7260
cttgcataca acagctatga agtccaggtc ccggtcctat tcccaaaaat aaggaatgga    7320
gaagtcacag acacctacga aaattactcg tttctaaatg ccagaaagtt agggggagat    7380
```

```
gtgcccgtgt atatctacgc tactgaagat gaggatctgg cagttgacct cttagggcta    7440
gactggcctg atcctgggaa ccagcaggta gtggagactg gtaaagcact gaagcaagtg    7500
accgggttgt cctcggctga aaatgccctg ctagtggctt tatttgggta tgtgggttac    7560
caggctctct caaagaggca tgtcccaatg ataacagaca tatataccat cgaggaccag    7620
agactagaag acaccaccca cctccagtat gcacccaacg ccataaaaac cgatgggaca    7680
gagactgaac tgaaagaact ggcgtcgggt gacgtggaaa aaatcatggg agccatttca    7740
gattatgcag ctgggggact ggagtttgtt aaatcccaag cagaaaagat aaaaacagct    7800
cctttgttta agaaaacgc agaagccgca aagggtatg tccaaaaatt cattgactca       7860
ttaattgaaa ataagaaga aataatcaga tatggttttgt ggggaacaca cacagcacta     7920
tacaaaagca tagctgcaag actggggcat gaaacagcgt ttgccacact agtgttaaag    7980
tggctagctt ttggagggga atcagtgtca gaccacgtca agcaggcggc agttgattta    8040
gtggtctatt atgtgatgaa taagccttcc ttcccaggtg actccgagac acagcaagaa    8100
gggaggcgat tcgtcgcaag cctgttcatc tccgcactgg caacctacac atacaaaact    8160
tggaattacc acaatctctc taaagtggtg gaaccagccc tggcttacct ccctatgct     8220 accagcgcat taaaaatgtt caccccaacg cggctggaga gcgtggtgat actgagcacc    8280
acgatatata aaacatacct ctctataagg aaggggaaga gtgatggatt gctgggtacg    8340
gggataagtg cagccatgga aatcctgtca caaaacccag tatcggtagg tatatctgtg    8400
atgttggggg taggggcaat cgctgcgcac aacgctattg agtccagtga acagaaaagg    8460
accctactta tgaaggtgtt tgtaaagaac ttccttggatc aggctgcaac agatgagctg    8520 gtaaagaaa acccagaaaa aattataatg gccttatttg aagcagtcca gacaattggt      8580
aaccccctga gactaatata ccacctgtat ggggttttact acaaaggttg ggaggccaag    8640
gaactatctg agaggacagc aggcagaaac ttattcacat tgataatgtt tgaagccttc    8700
gagttattag ggatggactc acaagggaaa ataaggaacc tgtccggaaa ttacattttg    8760
gatttgatat acggcctaca caagcaaatc aacagagggc tgaagaaaat ggtactgggg    8820
tgggcccctg cacccttag ttgtgactgg accccctagtg acgagaggat cagattgcca      8880
acagacaact atttgagggt agaaaccagg tgcccatgtg gctatgagat gaaagctttc    8940
aaaaatgtag gtggcaaact taccaaagtg gaggagagcg ggcctttcct atgtagaaac    9000
agacctggta ggggaccagt caactacaga gtcaccaagt attacgatga caacctcaga    9060
gagataaaac cagtagcaaa gttggaagga caggtagagc actactacaa aggggtcaca    9120
gcaaaaattg actacagtaa aggaaaaatg ctcttggcca ctgacaagtg ggaggtggaa    9180
catggtgtca taaccaggtt agctaagaga tatactgggg tcgggttcaa tggtgcatac    9240
ttaggtgacg agcccaatca ccgtgctcta gtggagaggg actgtgcaac tataaccaaa    9300
aacacagtac agtttctaaa aatgaagaag gggtgtgcgt tcacctatga cctgaccatc    9360
tccaatctga ccaggctcat cgaactagta cacaggaaca atcttgaaga gaaggaaata    9420
cccaccgcta cggtcaccac atggctagct tacaccttcg tgaatgaaga cgtagggact    9480
ataaaaccag tactaggaga gagagtaatc cccgaccctg tagttgatat caatttacaa    9540
ccagaggtgc aagtggacac gtcagaggtt gggatcacaa taattggaag ggaaaccctg    9600 atgcaacgg gagtgacacc tgtcttgaa aaagtagagc ctgacgccag cgacaaccaa      9660
aactcggtga agatcgggtt ggatgagggt aattacccag ggcctggaat acagacacat    9720
acactaacag aagaaataca caacagggat gcgaggccct tcatcatgat cctgggctca    9780
```

```
aggaattcca tatcaaatag ggcaaagact gctagaaata taaatctgta cacaggaaat    9840
gaccccaggg aaatacgaga cttgatggct gcagggcgca tgttagtagt agcactgagg    9900
gatgtcgacc ctgagctgtc tgaaatggtc gatttcaagg ggactttttt agataggag    9960 gccctggagg ctctaagtct cgggcaacct aaaccgaagc aggttaccaa ggaagctgtt   10020
aggaatttga tagaacagaa aaagatgtg gagatcccta actggtttgc atcagatgac    10080
ccagtatttc tggaagtggc cttaaaaaat gataagtact acttagtagg agatgttgga   10140
gagctaaaag atcaagctaa agcacttggg gccacggatc agacaagaat tataaaggag   10200
gtaggctcaa ggacgtatgc catgaagcta tctagctggt tcctcaaggc atcaaacaaa   10260
cagatgagtt taactccact gtttgaggaa ttgttgctac ggtgcccacc tgcaactaag   10320
agcaataagg ggcacatggc atcagcttac caattggcac agggtaactg ggagcccctc   10380
ggttgcgggg tgcacctagg tacaatacca gccagaaggg tgaagataca cccatatgaa   10440
gcttacctga agttgaaaga tttcatagaa gaagaagaga agaaacctag ggttaaggat   10500
acagtaataa gagagcacaa caaatggata cttaaaaaaa taaggtttca aggaaacctc   10560
aacaccaaga aaatgctcaa cccagggaaa ctatctgaac agttggacag ggaggggcgc   10620
aagaggaaca tctacaacca ccagattggt actataatgt caagtgcagg cataaggctg   10680
gagaaattgc caatagtgag ggcccaaacc gacaccaaaa cctttcatga ggcaataaga   10740
gataagatag acaagagtga aaaccggcaa aatccagaat tgcacaacaa attgttggag   10800
attttccaca cgatagccca acccaccctg aaacacacct acggtgaggt gacgtgggag   10860
caacttgagg cgggggtaaa tagaaagggg gcagcaggct tcctggagaa gaagaacatc   10920
ggagaagtat tggattcaga aaagcacctg gtagaacaat tggtcaggga tctgaaggcc   10980
gggagaaaga taaatatta tgaaactgca ataccaaaaa atgagaagag agatgtcagt   11040
gatgactggc aggcagggga cctggtggtt gagaagaggc caagagttat ccaataccct   11100
gaagccaaga caaggctagc catcactaag gtcatgtata actgggtgaa acagcagccc   11160
gttgtgattc caggatatga aggaaagacc cccttgttca acatctttga taagtgaga   11220 aaggaatggg actcgttcaa tgagccagtg gccgtaagtt ttgacaccaa agcctgggac   11280
actcaagtga ctagtaagga tctgcaactt attggagaaa tccagaaata ttactataag   11340
aaggagtggc acaagttcat tgacaccatc accgaccaca tgacagaagt accagttata   11400
acagcagatg tgaagtata tataagaaat gggcagagag ggagcggcca gccagacaca   11460
agtgctggca acagcatgtt aaatgtcctg acaatgatgt acggcttctg cgaaagcaca   11520
ggggtaccgt acaagagttt caacaggtg gcaaggatcc acgtctgtgg ggatgatggc   11580
ttcttaataa ctgaaaaagg gttagggctg aaatttgcta caaagggat gcagattctt   11640 catgaagcag gcaaacctca gaagataacg gaagggaaa agatgaaagt tgcctataga   11700
tttgaggata tagagttctg ttctcatacc ccagtccctg ttaggtggtc cgacaacacc   11760
agtagtcaca tggccgggag agacaccgct gtgatactat caaagatggc aacaagattg   11820
gattcaagtg gagagagggg taccacagca tatgaaaaag cggtagcctt cagtttcttg   11880
ctgatgtatt cctggaaccc gcttgttagg aggatttgcc tgttggtcct ttcgcaacag   11940
ccagagacag acccatcaaa acatgccact tattattaca aaggtgatcc aataggggcc   12000
tataaagatg taataggtcg gaatctaagt gaactgaaga gaacaggctt tgagaaattg   12060
gcaaatctaa acctaagcct gtccacgttg ggggtctgga ctaagcacac aagcaaaaga   12120
ataattcagg actgtgttgc cattgggaaa gaagagggca actggctagt taagcccgac   12180
```

-continued

```
aggctgatat ccagcaaaac tggccactta tacatacctg ataaaggctt tacattacaa    12240
ggaaagcatt atgagcaact gcagctaaga acagagacaa acccggtcat gggggttggg    12300
actgagagat acaagttagg tcccatagtc aatctgctgc tgagaaggtt gaaaattctg    12360
ctcatgacgg ccgtcggcgt cagcagctga gacaaaatgt atatattgta aataaattaa    12420
tccatgtaca tagtgtatat aaatatagtt gggaccgtcc acctcaagaa gacgacacgc    12480
ccaacacgca cagctaaaca gtagtcaaga ttatctacct caagataaca ctacatttaa    12540
tgcacacagc actttagctg tatgaggata cgcccgacgt ctatagttgg actagggaag    12600
acctctaaca gcccccgcgg atctagagga gcatgcgacg tcaggtggca cttttcgggg    12660
aaatgtgcgc ggaacccta tttgtttatt tttctaaata cattcaaata tgtatccgct    12720
catgagacaa taaccctgat aaatgcttca ataatattga aaaggaaga gtatgagtat    12780
tcaacatttc cgtgtcgccc ttattccctt ttttgcggca ttttgccttc ctgttttgc    12840
tcacccagaa acgctggtga agtaaaaga tgctgaagat cagttgggtg cacgagtggg    12900
ttacatcgaa ctggatctca acagcggtaa gatccttgag agttttcgcc ccgaagaacg    12960
ttttccaatg atgagcactt ttaaagttct gctatgtggc gcggtattat cccgtattga    13020
cgccgggcaa gagcaactcg gtcgccgcat acactattct cagaatgact tggttgagta    13080
ctcaccagtc acagaaaagc atcttacgga tggcatgaca gtaagagaat tatgcagtgc    13140
tgccataacc atgagtgata acactgcggc caacttactt ctgacaacga tcggaggacc    13200
gaaggagcta accgcttttt tgcacaacat ggggatcat gtaactcgcc ttgatcgttg    13260
ggaaccggag ctgaatgaag ccataccaaa cgacgagcgt gacaccacga tgcctgtagc    13320
aatggcaaca acgttgcgca aactattaac tggcgaacta cttactctag cttcccggca    13380
acaattaata gactggatgg aggcggataa agttgcagga ccacttctgc gctcggccct    13440
tccggctggc tggtttattg ctgataaatc tggagccggt gagcgtgggt ctcgcggtat    13500
cattgcagca ctggggccag atggtaagcc ctcccgtatc gtagttatct acacgacggg    13560
gagtcaggca actatggatg aacgaaatag acagatcgct gagataggtg cctcactgat    13620
taagcattgg taactgtcag accaagttta ctcatatata ctttagattg atttaaaact    13680
tcattttta tttaaaagga tctaggtgaa gatccttttt gataatctca tgaccaaaat    13740
cccttaacgt gagttttcgt tccactgagc gtcagacccc gtagaaaaga tcaaaggatc    13800
ttcttgagat cctttttttc tgcgcgtaat ctgctgcttg caaacaaaaa aaccaccgct    13860
accagcggtg gtttgtttgc cggatcaaga gctaccaact cttttccga aggtaactgg    13920
cttcagcaga gcgcagatac caaatactgt ccttctagtg tagccgtagt taggccacca    13980
cttcaagaac tctgtagcac cgcctacata cctcgctctg ctaatcctgt taccagtggc    14040
tgctgccagt ggcgataagt cgtgtcttac cgggttggac tcaagacgat agttaccgga    14100
taaggcgcag cggtcgggct gaacggggg ttcgtgcaca cagcccagct tggagcgaac    14160
gacctacacc gaactgagat acctacagcg tgagctatga aaagcgcca cgcttcccga    14220
agggagaaag gcggacaggt atccggtaag cggcagggtc ggaacaggag agcgcacgag    14280
ggagcttcca gggggaaacg cctggtatct ttatagtcct gtcgggtttc gccacctctg    14340
acttgagcgt cgatttttgt gatgctcgtc agggggggcgg agcctatgga aaacgccag    14400
caacgcggcc tttttacggt tcctggcctt ttgctggcct tttgctcaca tgttctttcc    14460
```

```
tgcgttatcc cctgattctg tggataaccg tattaccgcc tttgagtgag ctgataccgc    14520
tcgccgcagc cgaacgaccg agcgcagcga gtcagtgagc gaggaagcgg aagagcgc      14578
```